United States Patent [19]

Horling

[11] 4,034,611

[45] July 12, 1977

[54] PARTICULATE SAMPLING PROBE

[75] Inventor: James E. Horling, Rahway, N.J.

[73] Assignee: The United States of America as represented by the Secretary of the Navy, Washington, D.C.

[21] Appl. No.: 747,453

[22] Filed: Dec. 3, 1976

[51] Int. Cl.² .......................................... G01N 1/24
[52] U.S. Cl. .......................................... 73/421.5 R
[58] Field of Search ................ 73/421.5 R, 421.5 A

[56] References Cited

U.S. PATENT DOCUMENTS

| 3,511,099 | 5/1970 | Harsha | 73/421.5 A |
| 3,921,458 | 11/1975 | Logan | 73/421.5 R |

FOREIGN PATENT DOCUMENTS

| 345,214 | 1972 | U.S.S.R. | 73/421.5 R |

Primary Examiner—S. Clement Swisher
Attorney, Agent, or Firm—R. S. Sciascia; Henry Hansen

[57] ABSTRACT

A particulate sampling probe comprising an L-shaped protective tube of circular cross-section, and an intermediate tube and an inner collecting tube both of circular cross-section and concentrically disposed therein. The protective tube has an opening in one end permitting the entry of particulates into the collecting tube which communicates with the opening. A suction pump pulls particulates into the collecting tube. Exhaust from the collecting tube passes through a particulate collector, the pump, and a gas meter. Cooling air is introduced into the space between the protective tube and the intermediate tube near the collector, and exits from the protective tube from orifices near the opening in the protective tube. After a test, the preweighed collecting tube is removed from the protective tube and weighed. The difference between the pretest and posttest weights of the collecting tube and collector is a measure of the amount of particulates that has been sampled.

14 Claims, 3 Drawing Figures

PARTICULATE SAMPLING PROBE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to gas sampling devices, and more particularly to probes for use in sampling particulates in air.

In sampling engine exhaust, such as aircraft turbine engine exhaust, for the purpose of determining the particulate concentration in the exhaust, exhaust samples have been drawn through a hollow probe, whose upper portion has been bent at a right angle, to a particulate collector. A flexible line connects the probe to the particulate collector. Under test, a continuous sample of the exhaust is taken for a fixed period of time, such as an hour. During this time, an unknown amount of particulate material adheres to the inner walls of the probe and the flexible line. After the test, when the engine is shut down, the probe and line are removed from the engine along with the particulate collector. The particulate material should be removed as completely as possible from the inside of the probe and line, in order to obtain uniform results in successive measurements and prevent interference by particulates left over from previous tests with intake and passage of particulates in a subsequent test. Also, particulates in the exhaust sample which are deposited in the sampling probe will not be accounted for by the particulate collector, although these particulates were in the exhaust sample taken. Removal of the particulate material residue in the sample line can be accomplished by pouring small amounts of a solvent such as chloroform into one end of the probe and line and swirling it back and forth therein. The solvent is then poured into a clean glass or plastic bottle. This procedure is repeated until the solvent appears clean after the probe and line, usually requiring several washings. In the laboratory the probe and line washings are poured into a preweighed clean glass beaker. Additional chloroform is used to wash out the inside of the sample bottle. The solvent is then allowed to evaporate, after which the beaker and residue are weighed. The difference between tare and gross weight of the beaker indicates the amount of material accumulation in the probe and sample line. This process requires that the probe and line be completely removed from the engine and taken to an area where they can be washed out. Furthermore, a quantity of chloroform or other solvent must be available at the test site to wash out the probe and line. Chloroform in particular should be used only if there is adequate ventilation to avoid prolonged inhalation of its vapor. It is also highly flammable. Also, during the probe and line washing procedure, spillage of the solvent/particulate solution is a possibility, as is the uncertainty of removing all particulate material from inside the probe and line. Either possibility could compromise the validity of the final weight of the collected particulate material. In addition, 2 to 3 days are required for the solvent to completely evaporate, after which the beaker must be weighed again. Thus, the entire procedure requires a substantial amount of time.

SUMMARY OF THE INVENTION

Accordingly, it is a general purpose of the present invention to provide a particulate sampling probe which is capable of channeling a sample of emissions or other gas to a particulate collector for the purpose of determining the particulate concentration of the gas.

Other objects of the present invention are to provide a particulate sampling probe which is simple to use, enables accurate particulate measurement, and minimizes sample handling induced measurement errors such as inaccuracies due to spillage and loss of particulates or of particulate-bearing solvent.

Further objects of the present invention are to provide a particulate sampling probe whose particulate test residue can be readily, quickly and accurately measured.

Still further objects of the present invention are to provide a particulate sampling probe which eliminates the need for having chloroform or other solvent at the test site, need not be completely disassembled after test so that the amount of particulate residue therein can be determined, and can be used with any emission source or particulate collector.

Briefly, these and other objects of the invention are accomplished by a particulate sampling probe which can be used for sampling exhaust gas produced by engines such as aircraft turbine engines. This probe includes an L-shaped protective tube of circular cross-section having an orifice for intake of engine exhaust, and an intermediate tube and an inner collecting tube also of circular cross-section and concentrically disposed within the protective tube. Cooling air is supplied by a separate line to the space between the protective and intermediate tubing and exits from a plurality of holes in the protective tubing near the orifice thereof. In use, the collecting tube is first weighed before insertion into the probe. The collecting tube communicates with the orifice in the protective tube, and exhaust samples are drawn through the collecting tube and then through a particulate collector by a suction pump. A gas meter indicates the volume of gas passed through the probe and collector during a test. After a test has been completed, the collecting tube is removed from the probe and again weighed. Another collecting tube is then inserted in the probe. The weight change of the collecting tube following the test, together with that of the particulate collector, gives an indication of the amount of particulates present in the engine exhaust. The gas meter can be used to determine the amount of particulates per unit volume present in the exhaust.

Other objects, advantages, and novel features of the invention will become apparent from the following detailed description of the invention when considered in conjunction with the accompanying drawings wherein:

DESCRIPTION OF THE PREFERRED EMBODIMENT

Figure 1:
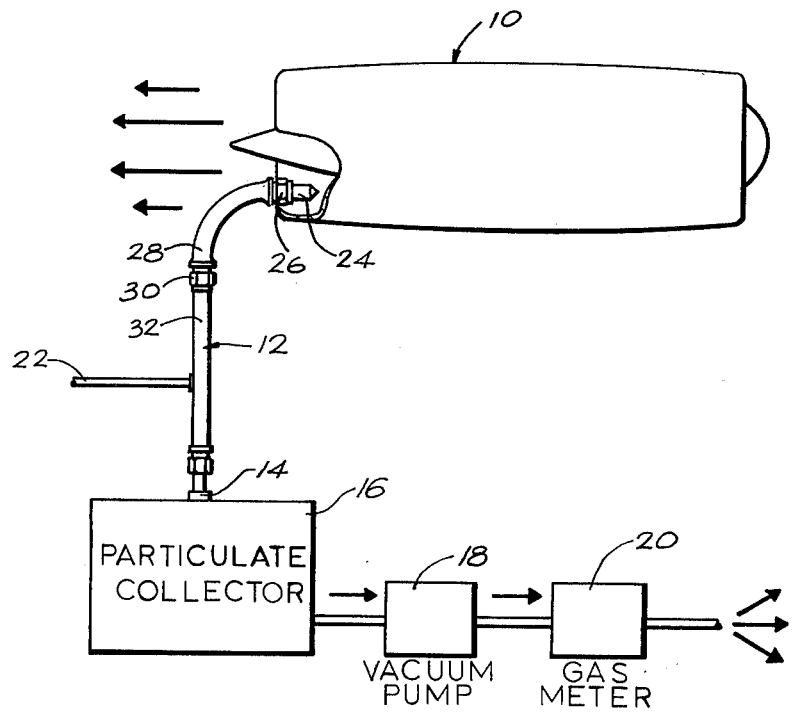
FIG. 1 shows a side elevation of a preferred embodiment of a particulate sampling probe according to the present invention installed in a jet engine with a particulate collector and other equipment, with a portion of the jet engine being cut away to show the position of the probe within the engine.

Referring now to the drawings, wherein like reference characters designate like or corresponding parts throughout the several views, there is shown in FIG. 1 an arrangement of a conventional jet engine 10 and the particulate sampling probe 12 of the present invention positioned behind the engine for sampling the exhaust of the engine for particulates and other substances while the engine is operating. Probe 12 is connected by bulkhead fitting 14 to a conventional particulate collector 16. Vacuum pump 18 draws an exhaust sample through probe 12 and collector 16. Gas meter 20 which is connected to vacuum pump 18 measures the volume of gas in the sample. Cooling air is supplied to probe 12 via line 22. Probe 12 includes probe tip 24 connected by compression-type tube fitting 26 to curved outer protective tubing 28. Tubing 28 is connected by compression-type tube fitting 30 to straight outer protective tubing 32 with which cooling air line 22 communicates. The base of probe 12 is connected by bulkhead fitting 14 to particulate collector 16. A portion of engine 10 has been cut away to better show the position of probe tip 24 therein for exhaust sampling.

Figure 2:
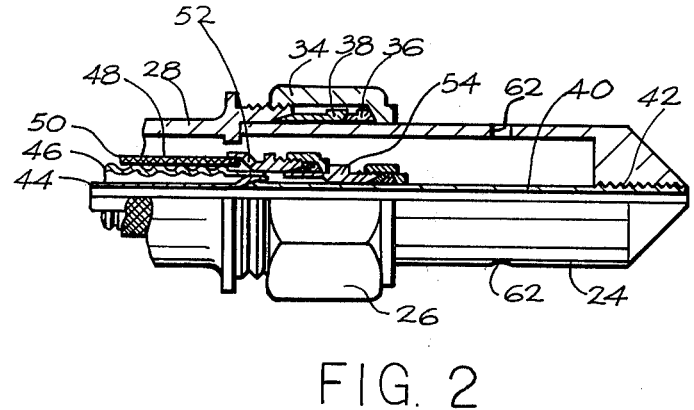
FIG. 2 is a portion of the probe of FIG. 1 shown in a quarter-sectional side view.

Probe tip 24 and other portions of probe 12 adjacent thereto are shown in greater detail in FIG. 2. In fitting 26, nut 34 threadingly engages outer tubing 28 and urges back ferrule 36 and front ferrule 38 against outer tubing 28 to connect probe tip 24 to outer tubing 28. Tip screw 40 disposed within probe tip 24 is hollow, includes at one end a threaded portion 42 which threadingly engages probe tip 24, and at its opposite end engages flexible collecting tube 44. Flexible collecting tube 44 can be fluoroelastomeric tubing, or alternatively can be flexible steel tubing. Collecting tube 44 extends continuously from tip screw 40 to particulate collector 16. Flexible tubing 44 is enclosed by flexible steel intermediate tubing 46 which in turn is enclosed by flexible metal hose connector 48. Connector 48 includes a braided wire sheath 50 enclosing flexible tubing 46 and a fitting 52 connected to compression-type reducer fitting 54 which engages tip screw 40.

Figure 3:
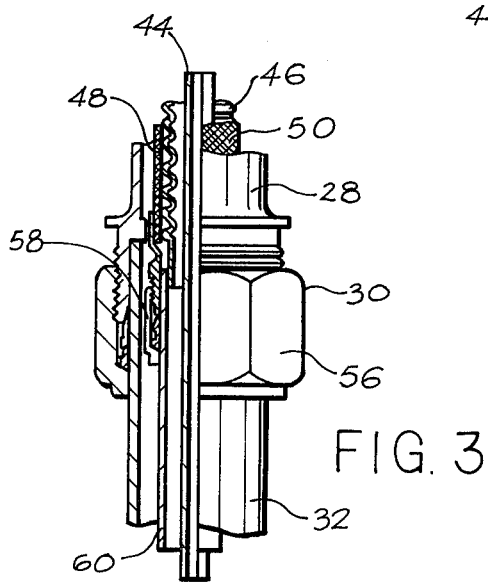
FIG. 3 is another portion of the probe of FIG. 1 shown in a quarter-sectional side view.

As shown in FIG. 3, straight outer tubing 32 is connected to curved outer tubing 28 by fitting 30 wherein nut 56 threadingly engages tubing 28. Compression-type fitting 58 of connector 48 connects connecter 48 and flexible intermediate tubing 46 to rigid intermediate tubing 60. Flexible collecting tube 44 passes within flexible intermediate tubing 46 and rigid intermediate tubing 60 to particulate collector 16.

Compression-type fittings 30, 52, 54, and 58 are similar in construction and operation to fitting 30.

The operation of particulate sampling probe 12 is as follows. Probe 12 is used to channel a sample of exhaust gas into a particulate collector 16 or other measuring device for the purpose of determining the particulate concentration in the engine 10 exhaust. Tip screw 40 and flexible collecting tube 44 are weighed before placement in probe 12 for sampling. During tests, engine 10 is operating and producing exhaust gas. For sampling engine 10 exhaust, probe 12 is positioned in the rear of engine 10 as shown in FIG. 1 so that probe tip 24 is positioned parallel to the direction of exhaust flow and tip screw 40 opens directly into the exhaust flow. Exhaust gas from engine 10 enters probe tip 24 through tip screw 40. The exhaust gas is drawn from tip screw 40 through flexible collecting tube 44 into particulate collector 16 by vacuum pump 18. Particulates still in the gas sample which have not adhered to the inside of tip screw 40 of collecting tube 44 are removed and collected in particulate collector 16. For example, particulate collector 16 can be a filter which is weighed before and after sampling to determine the weight of particulates collected during sampling. The gas then passes from particulate collector 16 through pump 18 to gas meter 20, which measures the volume of gas in the sample. From gas meter 20, the gas is then discharged into the open air. After the sample has been taken, such as by continuous sampling over a fixed period of time such as one hour, engine 10 is shut down and nut 56 is loosened to permit the portion of probe 12 above nut 56 to swivel away from engine 10. Nut 34 is then unscrewed from tubing 28, and probe tip 24 is unscrewed from tip screw 40 and removed from probe 12. Reducer 54 and fitting 52 are then unscrewed, and tip screw 40 and collecting tube 44 are then pulled out of probe 12 and weighed again. A new clean pre-weighed collecting tube 44 and tip screw 42 are then inserted in probe 12. Fitting 52 and reducer 54 are then retightened, probe tip 24 is threaded onto tip screw 40, and nut 34 is retightened on tubing 28. Probe 12 is then properly positioned in engine 10 and nut 56 is tightened, after which probe 12 is again ready for use. The difference between gross weight and tare weight of the tip screw 40 and collecting tube 44 indicates the amount of material accumulation in the tip screw 40 and in the collecting tube 44, and together with the amount of particulates collected by particulate collector 16 during sampling gives the total amount of particulates in the sample of exhaust gas taken.

To prevent overheating of and damage to collecting tube 44 by engine 10 and its exhaust, cooling air is supplied to probe 12 by line 22. Cooling air from line 22 enters straight outer protective tubing 32, but not rigid intermediate tubing 60 which line 22 does not penetrate. The cooling air travels in the space between outer tubing 32 and intermediate tubing 60 upwards into the space between outer tubing 28 and intermediate tubing 46 and therethrough to the space between probe tip 24 and tip screw 40. Cooling air exits probe 12 from a plurality of orifices 62 in probe tip 24.

Pressurized air can be used as cooling air for probe 12. However, to keep the pre-weighed collecting tube 44 and tip screw 40 clean and free from contamination that may be carried by the cooling air, it is necessary to keep cooling air away from them. Intermediate tubing 46 and 60 are used for this purpose.

Tip screw 40, probe tip 24, fittings 14, 26, 30, 52, 54 and 58, and tubing 28, 32 and 60 can be constructed from high-temperature material such as stainless steel. Tip screw 40 is a hollow rigid tube having threads 42 at one end for engaging probe tip 24 collecting tube 44 can be linked with particulate collector 16 for the introduction of particulate-bearing gas from tube to collector, by an adapter or any other conventional means.

It should be understood that, if high-grade nitrogen or bottled air were used for cooling, the intermediate tubing would not be needed to protect the collecting tube. Also, the size of the orifice or opening in the probe tip and tip screw through which the sample of exhaust gas must first enter the particulate sampling probe can be selected as desired or as required by various standards or governmental laws or regulations. In addition, the particulate sampling probe can be utilized to sample exhaust from any engine, to sample other emissions, and to sample ambient air. Furthermore, the particulate sampling probe can be used with any particulate collectors or other measuring device. Also, any type of airtight tube fitting can be used in the particulate sampling probe. For example, any compression-type or flare-end fittings could be used. In addition, the need for cooling air can be eliminated by using flexible steel tubing instead of fluoroelastomeric tubing for the collecting tube, provided that the other parts of the particulate sampling probe are made from high-temperature steel. Furthermore, any flexible tubing material which can withstand high temperatures and which will not be degraded by jet engine exhaust can be used instead of fluoroelastomeric tubing for the collecting tube.

Thus there has been provided a novel particulate sampling probe which is capable of channeling a sample of emissions or other gas into a particulate collector for the purpose of determining the particulate concentration of the gas. This particulate sampling probe can be used for sampling emissions or other gas for purposes other than measurement of particulate content, such as measurement of hydrocarbon content. The particulate test residue in the particulate sampling probe can be readily, quickly and accurately measured, without requiring a substantial amount of time for such measurement. Also, the particulate sampling probe is simple to use, enables accurate measurement of particulates in a gas sample, and minimizes sample handling induced measurement errors such as inaccuracies due to spillage and loss of particulates or of particulate-bearing solvent. In addition, the particulate sampling probe eliminates the need for having chloroform or other solvent at the test site, and need not be completely disassembled after test so that the amount of particulate residue therein can be determined.

Obviously, many modifications and variations of the present invention are possible in light of the above teachings. It is therefore to be understood that within the scope of the appended claims the invention may be practiced otherwise than as specifically described.

What is claimed is:

1. A particulate sampling probe for sampling particulates in a gas flow, comprising:
    an outer tube configured to extend one end thereof into a gas flow; and
    an inner tube removably disposed within the entire length of said outer tube, one end of said inner tube extending from the other end of said outer tube, said inner tube being at both ends for the passage of gas from said gas flow therethrough;
    said outer tube being configured at both ends to close about said inner tube.

2. A particulate sampling probe as defined in claim 1, further comprising:
    a cooling fluid line operatively connected to said outer tube for supplying cooling fluid to the space between said outer tube and said inner tube; and
    exhaust means operatively connected to said outer tube for removing said cooling fluid from the space between said outer tube and said inner tube.

3. A particulate sampling probe as defined in claim 2, wherein said outer tube has a plurality of holes comprising said exhaust means.

4. A particulate sampling probe as defined in claim 2, further comprising: an intermediate tube disposed between said outer tube and said inner tube.

5. A particulate sampling probe as defined in claim 1, wherein said inner tube comprises:
    a rigid tube, said outer tube being configured at said one end to close about one end of said rigid tube; and
    a flexible tube, one end of said flexible tube being releasably connected to the other end of said rigid tube, and the other end of said flexible tube extending from the other end of said outer tube.

6. A particulate sampling probe as defined in claim 5, wherein:
    said outer tube is threaded where it closes about said rigid tube; and
    said one end of said rigid tube is threaded to threadingly engage said outer tube.

7. A particulate sampling probe as defined in claim 5, wherein said rigid tube and said flexible tube are connected by a press joint.

8. A particulate sampling probe as defined in claim 1, further comprising:
    a particulate collector releasably and operatively connected to said one end of said inner tube; and
    a vacuum pump operatively connected to said collector for drawing gas through said inner tube and through said collector.

9. A particulate sampling probe as defined in claim 8, further comprising:
    a gas meter operatively connected to said pump for measuring the volume of gas drawn by said pump through said inner tube and said collector.

10. A particulate sampling probe as defined in claim 1, wherein said outer tube comprises:
    a gasket located at said other end of said outer tube and closing about said inner tube.

11. A particulate sampling probe as defined in claim 10, further comprising:
    a tube fitting attached to said inner tube and said gasket for holding said gasket in place.

12. A particulate sampling probe for sampling particulates in a gas flow, comprising:
    an outer tube configured to extend one end thereof into a gas flow;
    an inner tube removably disposed within the entire length of said outer tube, one end of said inner tube extending from the other end of said outer tube, said inner tube being open at both ends for the passage of gas from said gas flow therethrough; and
    an intermediate tube located between said outer tube and said inner tube and extending from said other end of said outer tube;
    said outer tube being configured at said one end to close about said inner tube and being configured at said other end to close about said intermediate tube.

13. A particulate sampling probe as defined in claim 12, wherein said outer tube comprises:
    a gasket located at said other end of said outer tube and closing about said intermediate tube.

14. A particulate sampling probe as defined in claim 13, further comprising:
    a tube fitting attached to said intermediate tube and said gasket for holding said gasket in place.

* * * * *